(12) United States Patent
Kwon

(10) Patent No.: US 7,182,747 B2
(45) Date of Patent: Feb. 27, 2007

(54) SOLID SOLUTION PERFORATOR FOR DRUG DELIVERY AND OTHER APPLICATIONS

(75) Inventor: Sung-Yun Kwon, Fremont, CA (US)

(73) Assignee: TheraJect, Inc., Fremont, CA (US)

( * ) Notice: Subject to any disclaimer, the term of this patent is extended or adjusted under 35 U.S.C. 154(b) by 0 days.

(21) Appl. No.: 11/285,669

(22) Filed: Nov. 21, 2005

(65) Prior Publication Data

US 2006/0074376 A1    Apr. 6, 2006

Related U.S. Application Data

(63) Continuation of application No. 10/767,359, filed on Jan. 28, 2004, which is a continuation of application No. 10/179,749, filed on Jun. 25, 2002, now Pat. No. 6,945,952.

(51) Int. Cl.
*A61B 17/20* (2006.01)
(52) U.S. Cl. .......................................... 604/46; 604/60
(58) Field of Classification Search ............... 604/46, 604/47, 48, 60, 890.1, 506, 93.01, 117, 180, 604/82–85, 131–147, 173–174, 181–182, 604/185, 187, 218, 239, 272–274; 424/426, 424/449, 448, 423, 400, 422
See application file for complete search history.

(56) References Cited

U.S. PATENT DOCUMENTS

| | | | |
|---|---|---|---|
| 3,072,122 A | * | 1/1963 | Rosenthal .................... 604/46 |
| 3,167,073 A | * | 1/1965 | Rosenthal .................... 604/46 |
| 3,596,660 A | * | 8/1971 | Melone ....................... 604/47 |
| 3,814,097 A | | 6/1974 | Ganderton et al. ......... 128/268 |
| 3,905,371 A | * | 9/1975 | Stickl et al. .................. 604/46 |
| 3,964,482 A | | 6/1976 | Gerstel et al. |
| 4,109,655 A | | 8/1978 | Chacornac |
| 4,592,753 A | | 6/1986 | Panoz |
| 4,798,582 A | | 1/1989 | Sarath et al. |
| 4,936,835 A | | 6/1990 | Haaga |
| 4,966,159 A | * | 10/1990 | Maganias ................... 600/556 |
| 5,250,023 A | | 10/1993 | Lee et al. |
| 5,262,128 A | | 11/1993 | Leighton et al. |

(Continued)

FOREIGN PATENT DOCUMENTS

| | | |
|---|---|---|
| JP | 2003-238347 | 8/2003 |
| JP | 2003238347 | 8/2003 |

*Primary Examiner*—Catherine S. Williams
(74) *Attorney, Agent, or Firm*—Robins & Pasternak LLP

(57) ABSTRACT

A solid drug solution perforator (SSP) system and an associated drug reservoir are provided for delivering therapeutic, prophylactic and/or cosmetic compounds, for nutrient delivery and for drug targeting. For drug delivery, the SSP system includes an active drug ingredient and a matrix of perforator material that biodegrades or dissolves quickly upon contact with a patient's body. The SSP system provides a skin barrier perforator and a controller for prompt initiation and cut-off of drug delivery. In a preferred method of transdermal drug delivery, an SSP system containing a selected drug penetrates into an epidermis or dermis, and the drug is promptly released from the (dissolving) SSP system perforator. An additional drug is optionally delivered from a patch reservoir through skin pores created by insertion of the perforator. Formulation and fabrication procedures for the SSP and associated reservoir are also provided. An SSP system can be fabricated with variety of shapes and dimensions.

23 Claims, 4 Drawing Sheets

U.S. PATENT DOCUMENTS

| | | | |
|---|---|---|---|
| 5,279,544 A | 1/1994 | Gross et al. | |
| 5,383,512 A | 1/1995 | Jarvis | |
| 5,445,611 A | 8/1995 | Eppstein et al. | |
| 5,457,041 A | 10/1995 | Ginaven et al. | |
| 5,458,140 A | 10/1995 | Eppstein et al. | |
| 5,527,288 A | 6/1996 | Gross et al. | |
| 5,591,139 A | 1/1997 | Lin et al. | |
| 5,695,484 A * | 12/1997 | Cox | 604/304 |
| 5,749,375 A | 5/1998 | Maginot | |
| 5,843,114 A | 12/1998 | Jang | |
| 5,848,991 A | 12/1998 | Gross et al. | |
| 5,855,211 A | 1/1999 | Nelson | |
| 5,855,801 A | 1/1999 | Lin et al. | |
| 5,879,326 A | 3/1999 | Godshall et al. | |
| 5,928,207 A | 7/1999 | Pisano et al. | |
| 5,983,136 A | 11/1999 | Kamen | |
| 6,013,050 A | 1/2000 | Bellhouse et al. | |
| 6,030,404 A | 2/2000 | Lawson et al. | |
| 6,050,988 A | 4/2000 | Zuck | |
| 6,083,196 A | 7/2000 | Trautman et al. | |
| 6,091,975 A | 7/2000 | Daddona et al. | |
| 6,102,896 A | 8/2000 | Roser | |
| 6,106,751 A | 8/2000 | Talbot et al. | |
| 6,132,755 A * | 10/2000 | Eicher et al. | 424/427 |
| 6,142,939 A | 11/2000 | Eppstein et al. | |
| 6,187,210 B1 | 2/2001 | Lebouitz et al. | |
| 6,219,574 B1 | 4/2001 | Cormier et al. | |
| 6,230,051 B1 | 5/2001 | Cormier et al. | |
| 6,256,533 B1 | 7/2001 | Yuzhakov et al. | |
| 6,312,612 B1 | 11/2001 | Sherman et al. | |
| 6,322,808 B1 | 11/2001 | Trautman et al. | |
| 6,331,266 B1 | 12/2001 | Powell et al. | |
| 6,331,310 B1 | 12/2001 | Roser et al. | |
| 6,334,856 B1 * | 1/2002 | Allen et al. | 604/191 |
| 6,352,506 B1 | 3/2002 | Eppstein et al. | |
| 6,352,722 B1 | 3/2002 | Blair | |
| 6,375,776 B1 | 4/2002 | Buoni et al. | |
| 6,379,324 B1 | 4/2002 | Gartstein et al. | |
| 6,406,455 B1 | 6/2002 | Willis et al. | |
| 6,440,096 B1 * | 8/2002 | Lastovich et al. | 604/27 |
| 6,485,453 B1 | 11/2002 | Buch-Rasmussen et al. | |
| 6,532,386 B2 | 3/2003 | Sun et al. | |
| 6,611,707 B1 | 8/2003 | Prausnitz et al. | |
| 6,743,211 B1 | 6/2004 | Prausnitz et al. | |
| 6,945,952 B2 * | 9/2005 | Kwon | 604/46 |
| 2001/0038858 A1 | 11/2001 | Roder et al. | |
| 2001/0053891 A1 | 12/2001 | Ackely | |
| 2002/0006355 A1 | 1/2002 | Whitson | |
| 2002/0009464 A1 | 1/2002 | Colaco | |
| 2002/0012687 A1 | 1/2002 | Roser et al. | |
| 2002/0016562 A1 | 2/2002 | Comier et al. | |
| 2002/0020688 A1 | 2/2002 | Sherman et al. | |
| 2002/0058067 A1 | 5/2002 | Blair | |
| 2002/0082543 A1 * | 6/2002 | Park et al. | 604/21 |
| 2002/0110585 A1 | 8/2002 | Godbey | |
| 2002/0146540 A1 | 10/2002 | Johnston et al. | |
| 2004/0049150 A1 * | 3/2004 | Dalton et al. | 604/46 |
| 2005/0065463 A1 | 3/2005 | Tobinaga et al. | |
| 2005/0137536 A1 * | 6/2005 | Gonnelli | 604/264 |

* cited by examiner

SOLID SOLUTION PERFORATOR FOR DRUG DELIVERY AND OTHER APPLICATIONS

CROSS-REFERENCE TO RELATED APPLICATIONS

This application is a continuation of U.S. patent application Ser. No. 10/767,359, filed Jan. 8, 2004, which is a continuation of U.S. patent application Ser. No. 10/179,749, filed Jun. 25, 2002, now U.S. Pat. No. 6,945,952, from which applications priority is claimed pursuant to 35 U.S.C. § 120, and which applications are incorporated herein by reference in their entireties.

FIELD OF THE INVENTION

This invention relates to controlled delivery of one or more drugs to, and diagnosis of fluids in, a patient's body.

BACKGROUND OF THE INVENTION

Many new drugs, including proteins, peptides and DNA constituents, have been developed for better and more efficient treatment for disease and illness. Especially due to recent advances in molecular biology and biotechnology, increasingly potent pharmaceutical agents, such as recombinant human insulin, growth hormone and erythropoeitin are available. However, a major limitation in using these new drugs is lack of an efficient drug delivery system; a drug must be transported across one or more biological barriers in the body at rates and in amounts that are therapeutically effective.

Most drugs are orally administered. However, some drugs, especially protein and peptide drugs, cannot be effectively adsorbed in this manner because of severe degradation in the gastrointestinal tract, poor absorption in intestinal membrane and/or first pass breakdown by the liver.

Another administration technique is parental injection, using standard syringes or catheters. Needle injection provokes needle phobia, substantial pain, local damage to the skin in many patients. Withdrawal of body fluids, such as blood, for diagnostic purposes provokes similar discomforts. Further, needle injection is not ideal for continuous delivery of a drug, or for continuous diagnosis.

Another drug delivery technique is transdermal delivery, which usually relies on diffusion of a drug across the skin. This method is not broadly applicable because of the poor skin permeability of many drugs. The outermost layer of skin, stratum corneum, represents a major barrier to transdermal drug penetration. Once a drug reaches the dermal depth (below the epidermal layer), the drug diffuses rapidly to deep tissue layers and other parts of the system via blood circulation.

In an attempt to improve the rate of drug delivery through the skin, chemical enhancers, iontophoresis, electroporation, ultrasound, and heat elements have been used to supplement drug delivery. However, these techniques are not suitable for some types of drugs and often fail to provide a therapeutic level of delivery. These techniques sometimes result in undesirable skin reactions and/or are impractical for continuous controlled drug delivery over a period of hours or days.

Other attempts, such as particle or liquid injection, have been made to design alternative techniques to transfer drugs transdermally. A main advantage of those techniques is absence of needle use and reduction of incidence of contamination. However, liquid injection frequently causes some pain and/or sub-dermal hemorrhage. One technique, ballistic particle injection, is hard to administer exactly and continuously and can cause micro-bleeding.

Other attempts, such as micro-needle drug delivery, have been developed using micro-fabrication procedures from the semiconductor industry. While the conventional devices have some uses, most of these devices are designed for drug delivery through a hollow interior of a needle or along an outer surface of a needle. However, because most of these needles are made from brittle silicon materials, needle breakage under the skin is a possibility. Some devices are used as skin perforators for subsequent patch drug application. There remains a need for better drug delivery devices that rely on smaller incisions, deliver drug with greater efficiency and less variability of drug administration, and/or are easier and safer for a patient to use.

What is needed is an approach that reduces or controls the skin barriers to permit controlled introduction of one, two or more drugs, simultaneously or sequentially, and to provide prompt initiation and cut-off of drug delivery with improved efficiency and safety.

SUMMARY OF THE INVENTION

These needs are met by the invention, which applies mechanical penetration of the skin, using a solid solution perforator ("SSP") system including an array of one or more needles, blades or other perforators that include a drug as part of a solid solution perforator and dissolve or undergo biodegradation relatively quickly. An "SSP device" optionally includes a reservoir of a second drug, contained in a patch, located adjacent to the perforator array and containing either the same drug as is contained in the SSP system perforators or a different drug. By creating a drug transport channel or port in the skin, especially in the outermost layer, through use of an SSP (system) perforator, the barrier properties of skin can be diminished or controlled for drug delivery and for providing access to body fluids to be monitored. Optionally, a patch includes a ring of adhesive that bonds with, and holds the reservoir against, the patient's skin adjacent to the perforated region of the skin. The patch system is separately activated to deliver the second drug through the skin channels(s) formed by the SSP perforator(s).

In contrast to conventional hollow needle technologies, the SSP system includes a solid matrix of dissolvable (including meltable) or biodegradable material that optionally holds one or more selected drugs and is formed into one or more perforators. The matrix can be composed of fast-dissolving and/or swelling materials. For drug delivery application, the SSP system includes an active drug that dissolves reasonably quickly and leaves the channel open for subsequent drug delivery, or to collect and monitor body fluids or other analytes. An SSP perforator can be 100 percent drug or a mixture of drugs, depending upon the application and physical/chemical properties of the drug(s). Inclusion of a swelling component in the matrix can keep the channel open even longer. The solid solution can be a homogeneous or non-homogeneous phase or porous solid solution, for example, a solid made from an emulsion or suspension.

DESCRIPTION OF BEST MODES OF THE INVENTION

Figure 1:
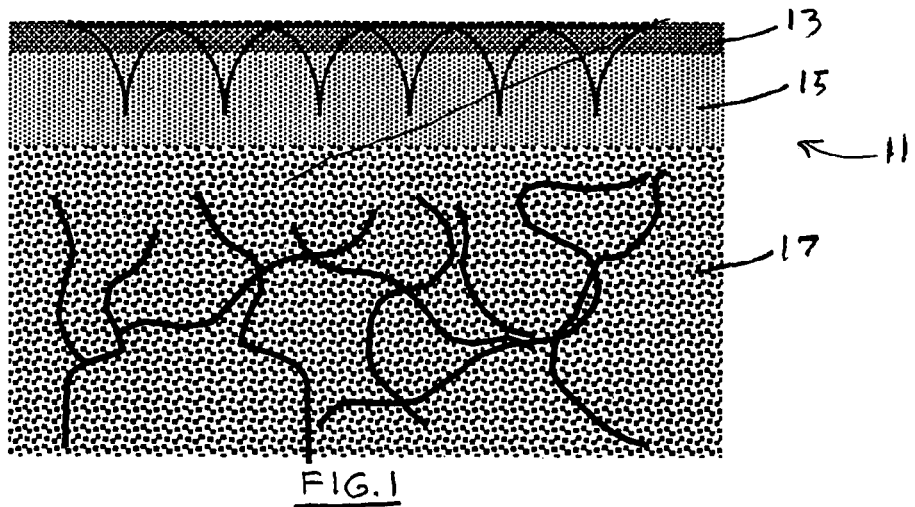
FIG. 1 is a schematic cross-section of a patient's skin.

FIG. 1 is a cross-sectional view of the top layers of the skin 11, including a stratum corneum 13, an epidermal layer or epidermis 15 and a dermal layer or dermis 17. The outermost layer of skin, the stratum corneum 13, is a dead cell layer, usually between 10 and 20 microns (μm) thick. The stratum corneum 13 contains hydrophilic keratinocytes surrounded by a hydrophobic extra-cellular matrix of lipids, mainly ceramide. Due to the structural and compositional uniqueness, the stratum corneum 13 presents the greatest barrier to transdermal flux of drugs or other molecules into the body, and of body fluids and other analytes out of the body. The stratum corneum 13 is continuously renewed by shedding of corneum cells, with an average turnover time of 2–3 weeks.

Below the stratum corneum 13 is the viable epidermis or epidermal layer 15, which is between 50 and 100 μm thick. The epidermis contains no blood vessels and freely exchanges metabolites by diffusion to and from the dermis 17, located immediately below the epidermis 15. The dermis is between 1 and 3 mm thick and contains blood vessels, lymphatics, and nerves. Once a drug reaches the dermal layer, the drug will perfuse through system circulation.

Figure 2A:
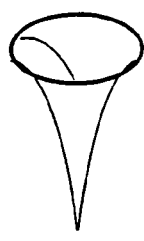
FIGS. 2A–2G are perspective views of examples of suitable SSP perforators that can be used in the invention.
Figure 2B:
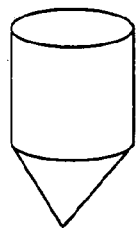
Figure 2C:
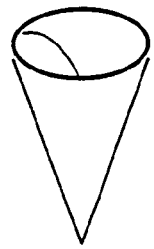
Figure 2D:
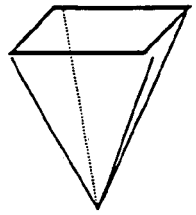
Figure 2E:
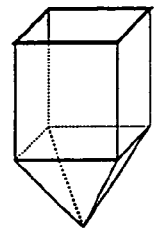
Figure 2F:
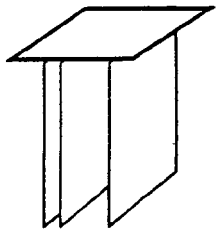
Figure 2G:
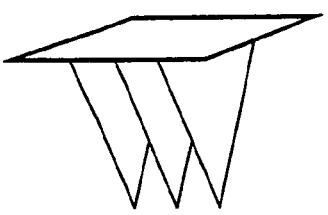

An SSP system includes one or more SSP drug perforators, preferably at least 20–200 in an area of about 1 cm$^2$, at least one or which is formed as a solid matrix of one or more needles or blades, each pointed or sharpened at a first end for perforation of the skin. Each perforator is strong and intact enough to pierce the stratum corneum, and is either biodegradable or dissolvable when the perforator (and drug) has penetrated into the patient's body with body fluid and/or solvent in the drug reservoir. The biodegradation or dissolution process may occur over a time interval of between a few tens of seconds and a few hours, with preference being given to shorter time intervals. FIGS. 2A–2G are perspective views of individual matrix shapes that are suitable for use with an SSP system. The matrix in FIG. 2A is a cone with a cusp-like point that may provide extra penetration power. The matrix in FIG. 2B is a conventional cone shape with a conventional linear penetration point. The matrices in FIGS. 2C and 2D are cylinder-plus-cone shape for a circular cylinder and for a rectangular (or, more generally, polygonal) cylinder, respectively. The matrix in FIG. 2E is a polygonal cone shape. The matrices in FIGS. 2F and 2G provide sequences of one or more sharp or slicing blades (straight or serrated) that contact and penetrate the skin. Other shapes with a pointed or blade end can also be used here. The SSP (system) perforators illustrated in FIGS. 2A–2G have various shapes and include the solid matrix material and the selected (first) drug within the matrix material (interstitially distributed or otherwise).

The SSP perforators can have straight or tapered shafts or can be pyramids or wedges or blades, as illustrated in FIGS. 2A–2G. In a preferred embodiment, the outer diameter of an SSP perforator is greatest at the base or second end, about 1–1000 μm, and the perforator outer diameter near the first end is preferably 10–100 μm. The length of an SSP perforator is typically in a range of 1–2000 μm, more preferably in a range of 100–1000 μm. The skin is not a smooth and rugged surface and has different depths microscopically. In addition, the thickness of the stratum corneum and elasticity of the skin varies from person to person and from location to location on any given person's body. A desirable penetration depth has a range, rather than a single value, for effective drug delivery and relatively painless and bloodless penetration. Penetration depth of an SSP perforator can affect pain as well as delivery efficiency. In certain embodiments, the perforator penetrates to a depth in the range of 10–1000 μm. In transdermal applications, the "penetrated depth" of the SSP perforator is preferably less than 100 μm so that a perforator, inserted into the skin through the stratum corneum, does not penetrate past the epidermis. This is an optimal approach to avoid contacting nerves and blood vessels. In such applications, the actual length of the SSP perforator can be longer because the basal layer associated with the SSP system may not be fully inserted into the skin because of elasticity and rough surface of the skin.

However, depending upon medical needs, perforator penetration to the dermis may be required in some applications. In these instances, use of a SSP system can be a practical option in handling instant drug delivery situations. The penetrating portion of an SSP perforator can be optimized by adjusting perforator variables (SSP length, dimension, mechanical properties of basal or substrate layer as Well as stroke and speed of insertion of an SSP perforator), as well as accounting for target skin elasticity, skin hardness and surface roughness.

A basal layer (shown in FIGS. 3 and 10) provides protection to isolate a perforated skin region from contamination, and the basal layer can contain anti-bacterial agents and can create occlusion to hydrate perforated skin to enhance flux of fluids. A portal channel likely will contract or expand depending on the perforator material properties after the SSP perforator dissolves or swells.

The primary functions of an SSP perforator are to pierce the stratum corneum, to provide prompt initiation and cut-off of drug delivery, and optionally to help keep the channel open for subsequent drug delivery or body fluid monitoring. As long as an SSP perforator dissolves reasonably quickly and is strong enough to pierce the stratum corneum, any biocompatible material can serve as an SSP perforator.

In preparing an SSP perforator, a mold is prepared using precision machining, micro-machining (such as MEMS), or laser-based or electro-discharge machining. When the mold is prepared, a liquid solution, including the matrix material and including the selected drug(s), is cast in the mold and dried. Depending on the viscosity and other physical and chemical properties of the liquid solution, additional force such as centrifuge force or compression force may be needed to fill the mold. To form a solid solution, the solvent needs to be air-dried, vacuum-dried or freeze-dried. Once a solid solution is formed, an SSP perforator is separated from the mold and cut to an appropriate shape and size.

Where a powder form is used for the SSP material, a mixed powder is spread over the mold. Depending upon the chemical and physical properties of the powder, appropriate heating of the powder may be applied to melt or insert viscous materials into the mold. Alternatively, the powder may be inserted into the mold by pressure and/or application of heating, with or without use of binding agents. When SSP perforators have been formed into an array, the SSP array is cooled, separated from the mold, and incorporated into an SSP system.

Another suitable approach for SSP fabrication is photo-cross linking. A polymer solution including a photo-initiator is cast on the mold and is solidified by irradiation. Once the solution is solidified, the solid solution can be peeled off and cut and shaped to appropriate size. Another feasible approach for making perforators is fabrication of a plurality of micro-fibers that are spooled, arrayed and combined in a plunger.

Suitable matrix materials for an SSP perforator include polymers, including but not limited to polyvinylpyrrolidone (PVP), polyethylene glycol (PEG), polyvinyl alcohol (PVA), cellulose, hydroxypropyl cellulose (HPC), hydroxyethyl cellulose (HEC), hydroxypropyl methylcellulose (HPMC), dextrin, mono- and polysaccharide, sodium carboxymethyl cellulose, polyalcohol, gelatin, gum arabic, alginate, chitosan cyclodextrin and other biopolymers.

Carbohydrate derivatives, such as sugar derivatives (trehalose, glucose, maltose, lactose, maltulose, iso-maltulose, lactulose, fluctose, turanose, melitose, melezitose, dextran, maltotol, sorbitol, xylitol, palatinit and mannitol) can be used. Water-soluble ingredients, such as phosphate, nitrate and carboxylate glasses, magnesium chloride, potassium chloride and calcium chloride can be also used for a matrix material, alone or mixed with a matrix polymer.

Other examples of suitable matrix materials include non-ionic hydrophilic or ionic surfactants or lipophilic additives selected from among alkylglucosides, alkylmaltosides, alkylthioglucosides, lauryl macrogolglycerides, polyoxyethylene alkyl ethers, polyoxyethylene alkylphenols, polyethylene glycol fatty acids esters, polyethylene glycol glycerol fatty acid esters, polyoxyethylene sorbitan fatty acid esters, polyoxyethylene-polyoxypropylene block copolymers, polyglycerol fatty acid esters, polyoxyethylene glycerides, polyoxyethylene sterols, derivatives, and analogues thereof, polyoxyethylene vegetable oils, polyoxyethylene hydrogenated vegetable oils, reaction mixtures of polyols and at least one member of the group consisting of fatty acids, glycerides, vegetable oils, hydrogenated vegetable oils, and sterols, tocopherol polyethylene glycol succinates, sugar esters, sugar ethers; sucroglycerides, and mixtures thereof.

An ionic surfactant may be selected from among alkyl ammonium salts; bile acids and salts, analogues, and derivatives thereof; fatty acid derivatives of amino acids, carnitines, oligopeptides, and polypeptides; glyceride derivatives of amino acids, oligopeptides, and polypeptides; acyl lactylates; mono-diacetylated tartaric acid esters of mono-diglycerides; succinylated monoglycerides; citric acid esters of mono-diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; and mixtures thereof.

A lipophilic additive is selected from among alcohols, polyoxyethylene alkylethers, fatty acids, bile acids, glycerol fatty acid esters, acetylated glycerol fatty acid esters, lower alcohol fatty acids esters, polyethylene glycol fatty acids esters; polyethylene glycol glycerol fatty acid esters, polypropylene glycol fatty acid esters, polyoxyethylene glycerides, lactic acid derivatives of mono/diglycerides, propylene glycol diglycerides, sorbitan fatty acid esters, polyoxyethylene sorbitan fatty acid esters, polyoxyethylene-polyoxypropylene block copolymers, transesterified vegetable oils, sterols, sterol derivatives, sugar esters, sugar ethers, sucroglycerides, polyoxyethylene vegetable oils, polyoxyethylene hydrogenated vegetable oils, reaction mixtures of polyols and at least one member of the group consisting of fatty acids, glycerides, vegetable oils, hydrogentated vegetable oils, and sterols, and mixtures thereof.

Figure 3:
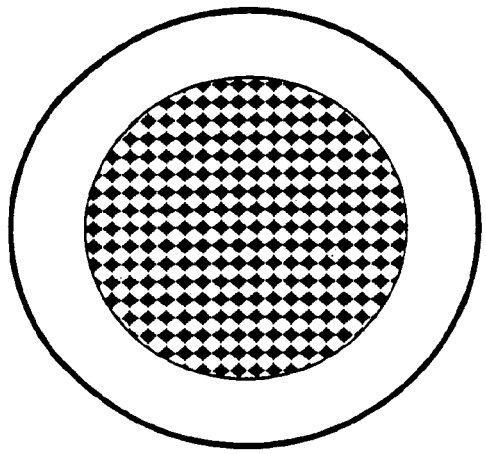
FIG. 3 is a plan view of an array of perforators and a surrounding annular ring of adhesive that are part of an SSP system.

FIG. 3 is a plan view of a patch system formed over an array of SSP perforators 31 that are optionally surrounded by a basal layer including an annular region 33 containing adhesive and an anti-bacterial agent (optional), to isolate the perforation region from other regions on the patient's skin. The annular region 33 of adhesive is intended to hold the SSP system to the skin and to prevent, or reduce the likelihood of, entry of foreign matter and/or external infection. Optionally, a drug reservoir (not shown in FIG. 3) may be located above the SSP perforator array 31 and/or may also be enclosed by the annular region 33 of adhesive.

Figure 4:
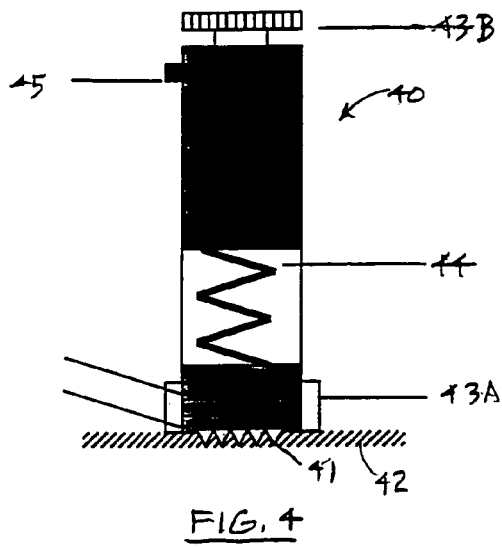
FIGS. 4–9 illustrate activation mechanisms that can be used for SSP skin penetration according to the invention.

FIG. 4 is a sectional side view illustrating a perforation activation mechanism 40 that causes one or more SSP perforators 41 to penetrate, or withdraw from, the patient's skin 42 to initiate and/or cut off delivery of a drug contained in the perforator(s). Initiation or cut off of drug delivery can occur in as little as about 5 minutes, by insertion or removal of the SSP perforator(s) 41. Depth of perforator penetration is adjusted by a perforation adjustment mechanism, 43A and 43B (optional), such as a knob or screw. An SSP perforator 41 is driven into the patient's skin 42 by a spring or similar mechanism 44 that is controlled by a perforation mechanism trigger 45.

Figure 5:
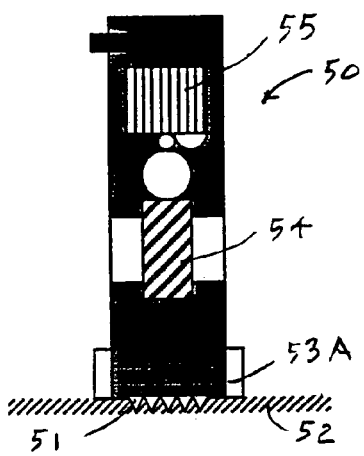

FIG. 5 is a sectional side view illustrating a perforation activation mechanism 50 in which one or more SSP perforators 51 is driven into, or withdrawn from, the patient's skin 52 by a screw 54 that is controlled by a screw knob or motor or similar device 55.

Figure 6:
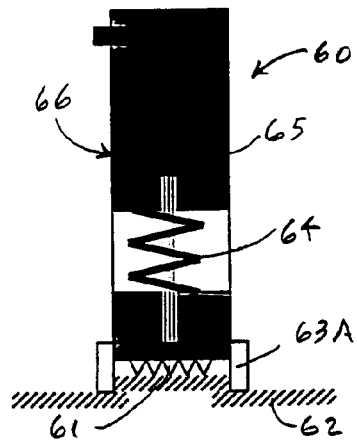

FIG. 6 is a sectional side view illustrating a perforation activation mechanism 60 in which one or more SSP perforators 61 is urged into the patient's skin 62 by a vacuum device 65, then injected by a spring 64 that causes the perforators 61 to be extended from, or withdrawn into, an activation housing 66. Application of a mild vacuum in the skin perforation region may help to reduce skin variability.

Figure 7:
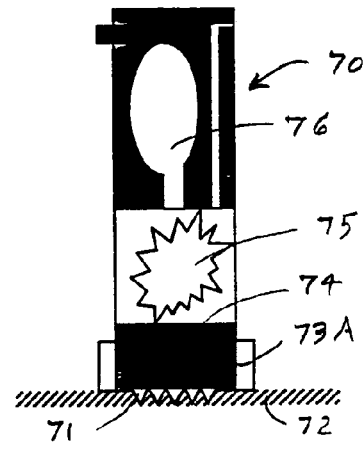

FIG. 7 is a sectional side view illustrating a perforation activation mechanism 70 in which one or more SSP perforators 71 is driven into, or withdrawn from, the patient's skin 72 by a gas expansion mechanism 74 including a gas pressure chamber 75 and a gas reservoir 76.

Figure 8:
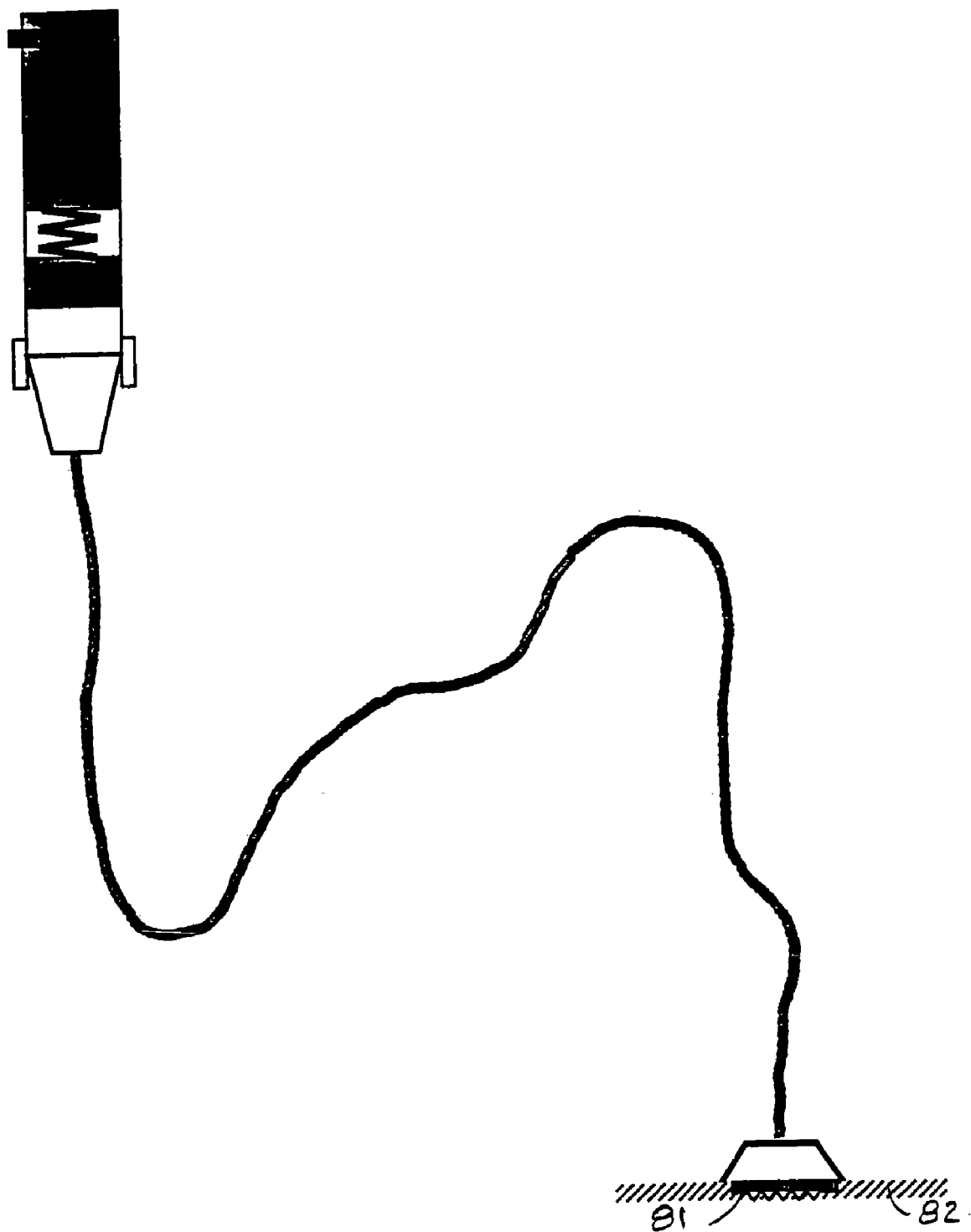

FIG. 8 illustrates one means by which the perforator mechanisms shown in FIGS. 4, 5, 6 and/or 7 may be used to control or vary movement, including but not limited to penetration depth, of the corresponding SSP perforators 82 into or out of the patient's skin 81. This design can be used with laparoscopes or endoscopes for internal drug delivery.

Figure 9:
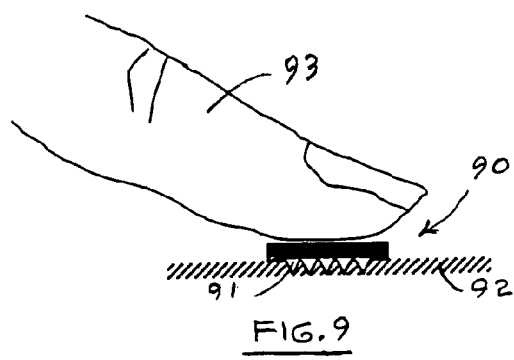

FIG. 9 is a sectional side view illustrating a perforation activation mechanism 90 in which one or more SSP perforators 91 is driven into the patient's skin 92 by pressure, manually applied by a finger or other pressure mechanism 93, to one side of the perforator(s).

Figure 10:
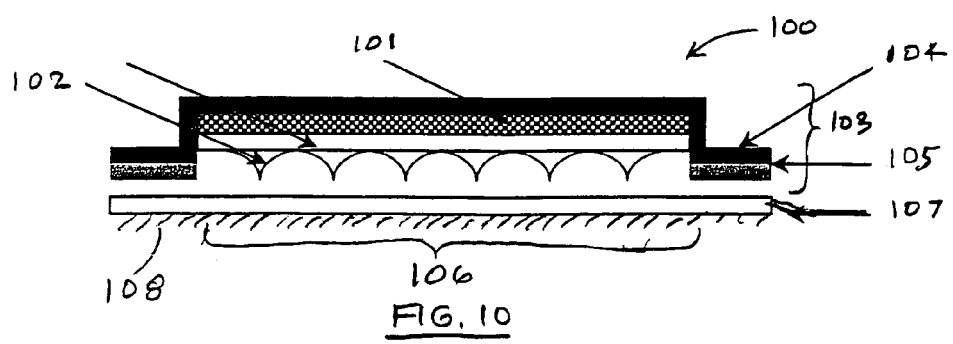
FIG. 10 illustrates a drug reservoir system according to the invention.

Optionally, a drug patch system 100, illustrated in FIG. 10, includes a drug reservoir 101, containing a second drug that may be the same as or different from the first drug, that is located above and adjacent to the SSP perforator array 102 and that has an independently controlled reservoir drug delivery system 103. The drug patch system 100 preferably includes a backing film 104 that surrounds the drug reservoir 101 and includes an annular adhesive region 105 (basal layer, best illustrated in FIG. 3) that surrounds and seals off the SSP skin perforation region 106. A plastic release liner 107 is peeled off before skin perforation and protects an SSP system until the liner is peeled off.

In a preferred embodiment, the reservoir in a patch system contains a drug and optionally contains a chemical enhancer in a liquid reservoir, a skin anti-irritant, an anti-infection chemical and/or other chemicals in liquid form. The chemical enhancer may be a fatty alcohol, an acid, an ester, a surfactant, a macrocyclis, a terpene, a phospholipid, a pyrrolidone, an amide or an amino acid. More particularly, a chemical enhancer may be drawn from among alkyl alcohol, alpha bisabodol, decyl alcohol, dexpanthenol, dodecanol, etylene glycol, fatty alcohols, glycerol, hexadecanol, isopropanol, octadecanol, tetrahydrofurfuryl alcohol, trichloroethanol, trifluoroethanol, alkyl acetamide, crotamiton, lauryl diethanolamide, toluamide, dimethyl acetamide, dimethyl formide, formamide, nicotainamide, acyl-amino-acids, alanine, arginine, proline, serine, aspartic acid, cysteine, glutamic acid, glycine, valine, leucine, isoleucine, protein aprotinin, azone, essential oils, such as carvone, cineole, eucalyptol, eugenol, methol, methone, terpene fatty acids, such as carboxyl acid, capric acid, diisopropyladipate, isopropyl myristate (IPM), isostearic acid, glyceryl monolaurate (GML), glycerol monooleate (GMO), lactic acid, linoleic acid, lauric acid, methyl laurate, methyl myristate, oleic acid, polyethylene glycol monolaurate, sorbitan monooleate (SMO), sucrose cocoate, sucrose monoloaurate, sucrose monooleate, triglyceride, macrocyclic enhancers, such as cyclodextrin, cyclopentadecanone and cyclopentadecanolide, phospholipids, phospholipid/phosphate enhancers, such as dialkylphospahte, lecithin, dioxane, dioxolane, alkylsulfones, alkylsulfones, cetyl ether, cyclic dimethylsiloxane, decamethyltetrasiloxane, dialkyl sulfoxides, dimethylsulfoxide, decylmethylsulfoxide, hexamethyldisiloxane, methyl octylsulfoxide, alkyl ammonium bromide, benzyl nicotinate, butylazocyclopentane, capsaicin, calcium thioglycolate, cyclic amine, diethyl sebacate, dimethylamino acetate, ethylene glycol monoethyl ether, imidazole, methylorthoformate, oxazoline, proline, urea, urethane, macrocyclis, amines, alkyl pyrolidones, N-methylpyrrolidone, ethyl pyrrolidone, pyrrolidone, hydroxymethylpyrrolidone, hexyl pyrrolidone, lauryl pyrrolidone, pyrrolidonecarboxylic acid, lauryl pyrrolidone carboxylic acid, pyroglutamic acid, sodium dedecyl sulfate, sodium deoxycholate, sodium lauryl sulfate, sorbitan monopalmitate, sorbitan trioleate, soybean casein, terpenes, piperazine derivatives, sodium traurocholate, liposome, bisbolol, dithiothreitol and vitamin E (α-tocopherol).

Figure 11A:
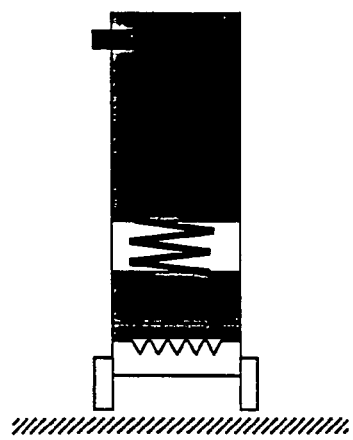
FIGS. 11A–11C and 12A–12F illustrate operation of patch systems that can be used as part of the invention.
Figure 11B:
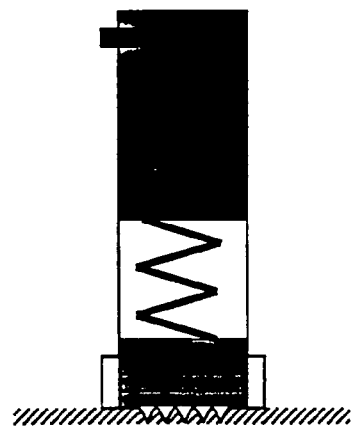
Figure 11C:
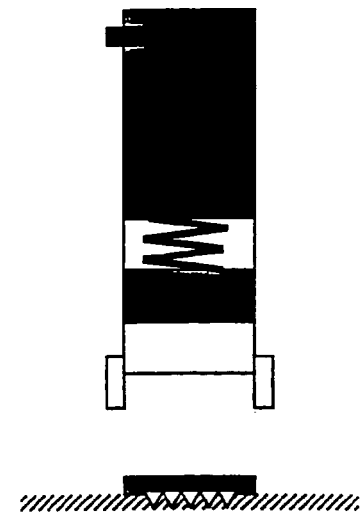

FIGS. 11A/11B/11C are sectional side views illustrating a preferred embodiment of an SSP patch insertion process in a transdermal application. In FIG. 11A, adhesive in a basal layer 111 of an SSP patch 110 is applied to the skin 112 to hold the patch against the skin. At this point, the perforators 113 are displaced from the skin 112. In FIG. 11B, a plunger or other mechanism 114 is activated to move the perforators 113 into contact with the skin 112, to penetrate the stratum corneum and to enter the epidermis or dermis. In FIG. 11C, the perforators 113 and a basal layer 115 remain in contact with the skin 112. In a preferred embodiment, drug molecules in a reservoir within the upper reservoir of the SSP patch system flow through the channel created by a fully or partially dissolved SSP perforator and into the epidermis. The drug molecules then diffuse into the dermis for local treatment or for transport through the body.

An SSP patch system preferably includes a reservoir containing a liquid or gel form of the second drug and one or more perforators extending from at least a part of the reservoir's surface. The SSP perforators associated with the patch system penetrate the stratum corneum of the skin to enhance percutaneous drug administration and to provide prompt drug delivery and/or prompt drug cut off. In the patch system, the SSP perforators and the reservoir can be constructed as a single unit or as separate units.

The patch reservoir is intended to provide sustained, controllable delivery of a liquid or semi-liquid (second) drug into or across a biological barrier so that diffusion channels are created and remain open after insertion and dissolution of an SSP perforator (matrix plus drug). The size, shape, composition and areal density of SSP perforators affect the drug release rate through the skin channels. Alternatively, other control mechanisms such as iontophoresis, sonophoresis, heating components and mechanical vibration forces can accelerate, decelerate or otherwise control drug transport through the stratum corneum.

An SSP patch system is applied to the skin so that one or more SSP perforators penetrate through the stratum corneum, into the epidermis or into the dermis depending on the application. In a preferred embodiment, drug molecules in a reservoir in an SSP patch system flow through the channel created by a fully or partially dissolved SSP perforator and into the epidermis or dermis. The drug molecules diffuse into the dermis for local treatment or for transport through the body.

An SSP system can transport therapeutic and/or prophylactic agents, including drugs and vaccine and other bioactive molecules, across skin and other tissues. An SSP device permits drug delivery and access to body fluids across skin or other tissue barriers, with minimal damage, pain and/or irritation at the tissue. In drug delivery applications, an SSP perforator optionally is primarily composed of an active drug and a dissolving or swelling solid matrix depending on a desired drug profile. The SSP system acts as immediate drug source and as a channel creator for subsequent drug delivery through skin. In a diagnostic application, an SSP perforator contains no drug and is composed substantially entirely of a fast-dissolving, biologically inactive solid or a dissolvable or swellable matrix for creating and maintaining the channels. Depending on the application, an osmotically active or anti-irritant compound can have a beneficial effect. In some diagnostic applications and SSP perforator can include or consist of sensor materials that react to presence of specific analytes.

A primary function of a basal layer in an SSP system with reservoir to separate the drug reservoir and to serve as a transport bridge between the reservoir and the remainder of the system. The basal layer material can be same as the solid matrix material, or may be a different material, depending on the application. In an SSP system without reservoir, the basal layer can be laminated with one or more additional layers or materials for controlled release. The outermost basal layer can act as an impermeable backing film to protect against any virus or bacterium that might otherwise invade the skin perforation region. In order to avoid back diffusion from other parts of the SSP system, this layer should have low drug solubility. Where additional and sustained drug release is required, the basal layer can be constructed to contain more of a drug or to provide a conduit to a secondary reservoir. It is useful to have anti-virus and/or anti-bacterial protection in the basal layer to suppress infection. In order to vary or control the drug delivery rate, an external physical enhancement system, using iontophoresis, or sonophoresis, piezoelectric response or a similar response, can be provided as part of a basal layer and/or an overlay layer.

Figure 12A:

FIG. 12A illustrates a simple design of an SSP patch 120A, including a basal layer 121 including a backing and an array of one or more perforators 122 located adjacent to the skin 123. Active ingredients (drug or drug solid solution) are contained in the perforator. The basal layer can have different thicknesses but is most often an impermeable backing layer. This design is ideal for potent drug delivery, for administrating small doses or for instant drug delivery.

Figure 12D:
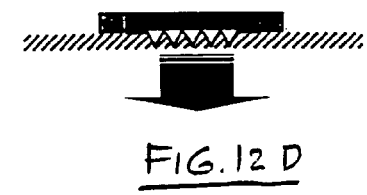
Figure 12B:

FIG. 12B illustrates another design of an SSP patch 120B, including an array of perforators 122 and a basal layer 124 that is porous and optionally serves as a drug reservoir. Active ingredients are contained in the perforator and in the basal layer. The basal layer 124 can have different composition from the SSP perforator(s) outermost layer but is most often an impermeable backing layer. This design is also ideal for potent drug delivery, for administrating small doses systemically, or for topical applications.

Figure 12E:
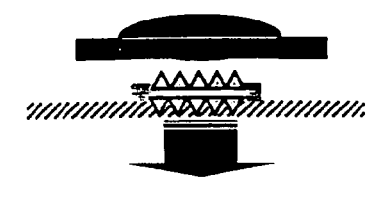
Figure 12C:
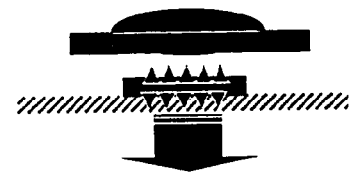

FIG. 12C illustrates a more complex design of an SSP patch 120C. Active ingredients are contained in the perforator and in the reservoir. A top portion of the basal layer 126 contains a drug reservoir patch 125. A first set of perforators 122-1 is oriented to penetrate the stratum corneum of the skin 123, and a second set of perforators 122-2 is oppositely oriented to penetrate a membrane that surrounds or contains fluid in the reservoir patch 125. The reservoir patch 125 can be applied after SSP system application or can be combined with SSP layers. The reservoir can have a variety of composition or formulation depending on targeted drug release profile.

FIGS. 12D and 12E illustrate other designs, 120D and 120E, of SSP patch systems modified from FIGS. 12B and 12C, respectively. The perforator does not contain any drug but does include a dissolving matrix; active ingredients are contained in the basal layer and/or reservoir only. Depending on the drug solubility and concentration, drug release from the basal layer can be controlled. The systems shown in FIGS. 12D and 12E are used primarily for diagnostic purposes and for sustained drug release applications, respectively.

Figure 12F:

FIG. 12F illustrates use of swellable materials as part of an SSP patch system 120F, optionally with no drug(s) included in the perforator solid matrix. This design extends skin channel openings for a longer (or shorter) time interval and extends the duration of drug delivery or is used for diagnostic applications.

Any drug or other bioactive agent can be delivered using the SSP system. Delivered drugs can be can be proteins, peptides, DNA, genes, polysaccharides, and synthetic organic and inorganic compounds. Representative agents include, but are not limited to, anti-infectives, hormones, growth regulators, drugs regulating cardiac action or blood flow, and drugs for pain control. The drug can be for local treatment or for regional or systemic therapy. The following are representative protein drug examples dose per injection they are used to treat:

| | |
|---|---|
| α-interferon | 11–100 µgm |
| β-interferon for multiple sclerosis | 22–44 µgm |
| Erythropoetin for anemia | 10–30 µgm |
| Follicle stimulating hormone (FSH) | 5–30 µgm |
| Granulocyte Colony Stimulating Factor (G-CSF) | 9–15 µgm |
| Granulocyte Macrophage Colony Stimulating Factor | 250 µgm |
| Human chorionic gonadotropin | 30–300 µgm |
| Leutinizing hormone | 2–30 µgm |
| Salmon Calcitonin | 25–50 µgm |
| Glucagon | 1 mgm |
| GNRH antagonist | 2 mgm |
| Insulin | 0.75–1.5 mgm |
| Human Growth Hormone (GHD) | 0.25–1.5 mgm |
| Human Growth Hormone (AIDS) | 6 mgm |
| Testerone | 5–10 mgm |

-continued

| | |
|---|---|
| Lidocaine | 2–5 percent |
| Diclofenac Sodium | 100 200 mgm |
| Oxybutynin | 5–15 mgm |
| Ketoprofen | 75–200 mgm |
| Alemdronate | 10 mgm |
| Enalpril Maleate | 10–40 mgm |
| Phenylpropanolamine HCl | 75 mgm |
| Cromolyn sodium | 3.2–10 mgm |
| Isotretinoin | 0.5–2 mgm/Kgm |
| Oxytocin | 1–2 unit/min/iv |
| Paroxetine HCl | 20 mgm |
| Flurbiprofen | 100 mgm |
| Sertaline | 50 mgm |
| Venlafaxine | 75 mgm |
| Leuprolide | 0.125–0.25 mgm |
| Risperidone | 4–6 mgm |
| Galanthamine hydrobromide | 16–24 mgm |
| Enoxaprin, anticoagulant | |
| Etanercept, rheumatoid arthritis | |
| Fentanyl, postoperative and chronic pain | |
| Filgrastin, low white blood cells from chemotherapy | |
| Heparin, anticoagulant | |
| Parathyroid hormone (PTH) | |
| Somatropin, growth hormone | |
| Sumatriptan, migraine headaches | |
| Morphine | |
| Opiate anti-arthritis. | |

Many drugs can be delivered at a variety of therapeutic rates, controlled by varying a number of design factors including: dimensions of the SSP, dissolving rate of the matrix, number of SSP perforators, size of the SSP patch, size and composition of the reservoir, and frequency of using the device. For example, devices designed to deliver drug at high rates might have a more active drug loaded SSP and/or a faster dissolving matrix. For sustained drug release, fewer SSP perforators and/or use of a slow(er) dissolving solid matrix are useful. The SSP patch can be applied to the skin or other tissue to deliver drugs continuously or intermittently or at a varying rate, for time intervals ranging from a few seconds to several hours or days. Most applications of SSP drug transdermal delivery would target the epidermis, although delivery into blood stream directly is available by extending the penetration length of an SSP patch.

The SSP patch systems disclosed herein are also useful for controlling transport across tissues other than skin. For example, an SSP patch can be inserted into a patient's eye to control or correct conjunctiva, sclera, and/or cornea problems, to facilitate delivery of drugs into the eye with a slow moving actuator. Similarly, an SSP system, inserted into the eye, could facilitate transport of fluid out of the eye, which may be of benefit for treatment of glaucoma. An SSP patch can also be inserted into the buccal (oral), nasal or vaginal regions or inside a tissue with the aid of a laparoscope or into other accessible mucosal layers to facilitate transport into or across those tissues. For example, a drug may be delivered across the buccal mucosal for local treatment in the mouth. As another example, SSP systems may be used internally within the body on, for example, the lining of the gastrointestinal tract to facilitate uptake of orally-ingested drugs or at the lining of blood vessels to facilitate penetration of drugs into the vessel wall. In this case of internal tissue application, use of bio-adhesive SSP material can be an additional benefit.

Another important application is vaccination. The skin is an ideal site for effective vaccine delivery because it contains a network of immune cells, such as Langerhans cells. There are several advantages of SSP technology in delivering antigenic compounds to the epidermis, which has a high density of immune cells and consequently triggers the immune system more effectively. An SSP system is a practical design for developing multivalent vaccines easily and is expected to provide more stability than use of a liquid for transport and storage of drugs. The following vaccines can be delivered, among others.

Hepatitis B
HIV vaccine
Influenza
Diphtheria
Tetanus
Pertussis
Lyme disease
Rabies
Pneumococcus
Yellow fever
Cholera
Vaccinia
Tuberculosis
Rubella
Measles
Mumps
Rotavirus
Botulinum
Herpes virus
Other DNA vaccines Another area of applications is cosmeceutical. An SSP system including a patch can deliver botox toxin or a hydroxyacid more efficiently and safely to remove or reduce wrinkle formation and skin aging. The system is also useful for treating lesions or abnormal skin features, such as pimples, corns, warts, calluses, bunions, actinic keratoses and hard hyperkeratotic skin, which is often found on the face, arms, legs or feet. An SSP system is also useful as a food patch to deliver essential amino acids, fats and vitamins. A food patch is often used in emergencies.

What is claimed is:

1. An array comprising a plurality of dissolvable, substantially solid, drug solution delivery perforators, wherein each perforator comprises a first end with at least one point or blade adapted for penetrating skin and for providing a skin aperture on a patient's body, and further wherein at least one of the perforators is formed from a matrix material that comprises sodium carboxymethyl cellulose, is dissolvable and includes a first selected drug distributed within the matrix, the perforators dissolving over a time interval of between a few tens of seconds and a few hours after the perforator has been inserted into a patient's body.

2. The array of claim 1, wherein the first drug is at least one of a protein, a peptide, a DNA component, a gene, a polysaccharide, a vaccine, a synthetic organic compound and a synthetic non-organic compound.

3. The array of claim 1, wherein said first end of said perforator is a needle having a cross-sectional shape that is cusp-like.

4. The array of claim 1, wherein said perforator has an outer diameter near said first end in a range of 10–100 μm.

5. The array of claim 1, wherein said array comprises at least 20 of said dissolvable perforators in a region having an area no more than 1 $cm^2$.

6. The array of claim 1, further comprising a fluid reservoir, in fluid communication with said skin aperture and having a fluid container adapted for receiving and holding a selected amount of a solvent for dissolving said perforator.

7. The array of claim 1, further comprising a fluid reservoir, in fluid communication with said skin aperture and having a fluid container adapted for receiving and holding a selected amount of a second selected drug.

8. The array of claim 7, wherein said reservoir comprises a patch reservoir that receives and holds said second drug, and said first and second drugs are substantially the same.

9. The array of claim 7, wherein said reservoir comprises a patch reservoir that receives and holds said second drug, and said first and second drugs are different from each other.

10. The array of claim 7, wherein said reservoir comprises a patch reservoir having a region of adhesive that surrounds and contacts a selected region on said patient's skin.

11. The array of claim 10, wherein said adhesive comprises a substance that is anti-bacterial.

12. The array of claim 7, wherein said reservoir contains a fluid comprising a chemical enhancer selected from the group consisting of a fatty alcohol, an acid, an ester, a surfactant, a macrocyclis, a terpene, a phospholipid, a pyrrolidone, an amide and an amino acid.

13. A method of delivering one or more drugs to a patient, said method comprising:

(a) contacting the array of claim 7 with a patient's skin; and (b) causing at least one perforator in the array to penetrate the patient's skin, to deliver one or more drugs to the patient.

14. The method of claim 13, wherein diffusion channels are created by dissolution of said perforators and said second selected drug diffuses through said diffusion channels.

15. The method of claim 13, wherein the array is contacted with buccal mucosa.

16. The method of claim 13, wherein the one or more drugs is a cosmeceutical.

17. A method of delivering one or more drugs to a patient, said method comprising:

(a) contacting the array of claim 1 with a patient's skin; and (b) causing at least one perforator in the array to penetrate the patient's skin, to deliver one or more drugs to the patient.

18. The method of claim 17, wherein said at least one perforator in the array is caused to penetrate the patient's skin by manual pressure.

19. The method of claim 17, wherein said at least one perforator is positioned to penetrate said skin to an epidermal layer of said skin.

20. The method of claim 17, wherein said at least one perforator is positioned to penetrate said skin to a dermal layer of said skin.

21. The method of claim 17, wherein said at least one perforator penetrates said patient's skin to a distance in a range of 10–1000 μm.

22. The method of claim 17, wherein the array is contacted with buccal mucosa.

23. The method of claim 17, wherein the one or more drugs is a cosmeceutical.

* * * * *